(12) United States Patent
Hauger et al.

(10) Patent No.: US 9,788,718 B2
(45) Date of Patent: Oct. 17, 2017

(54) SURGICAL MICROSCOPE

(71) Applicant: Carl Zeiss Meditec AG, Jena (DE)

(72) Inventors: Christoph Hauger, Aalen (DE); Artur Hoegele, Oberkochen (DE); Peter Reimer, Ellwangen (DE); Holger Matz, Unterschneidheim (DE); Joachim Steffen, Westhausen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/260,108

(22) Filed: Sep. 8, 2016

(65) Prior Publication Data

US 2017/0065172 A1 Mar. 9, 2017

(30) Foreign Application Priority Data

Sep. 8, 2015 (DE) ........................ 10 2015 115 106

(51) Int. Cl.
*A61B 3/14* (2006.01)
*A61B 3/10* (2006.01)
(Continued)

(52) U.S. Cl.
CPC ............ *A61B 3/103* (2013.01); *A61B 3/0025* (2013.01); *A61B 3/0041* (2013.01);
(Continued)

(58) Field of Classification Search
USPC .................................. 351/206, 215, 216, 221
See application file for complete search history.

(56) References Cited

U.S. PATENT DOCUMENTS 5,841,149 A 11/1998 Spink et al.
5,953,114 A 9/1999 Spink et al.
(Continued)

FOREIGN PATENT DOCUMENTS

DE 10009532 8/2001
DE 103 00 925 A1 9/2003
(Continued)

OTHER PUBLICATIONS

Gross, H., "Inverse Problems in Classical Optics", English translation of Carl Zeiss AG presentation, dated Oct. 5, 2004, pp. 1 to 44.

*Primary Examiner* — Mohammed Hasan
(74) *Attorney, Agent, or Firm* — Walter Ottesen, P.A.

(57) ABSTRACT

A surgical microscope for imaging structures of an eye includes: a front optical unit, an illumination device which has an illumination-radiation-emitting illumination source and which illuminates the retina of the eye with an illumination spot via an illumination beam path which extends through the front optical unit, a camera and an adjustable camera optical unit disposed upstream thereof, an imaging beam path which extends through the front optical unit and the camera optical unit, and a control device which controls the camera optical unit and sets the latter in such a way that the retina of the eye in the region of the illumination spot is imaged on the camera. The control device varies a focusing state of the camera optical unit and, as a result thereof, records a plurality of images of the retina in the region of the illumination spot, the images being focused in different depth planes, and establishes a refractive value of the eye from these images.

12 Claims, 2 Drawing Sheets

(51) Int. Cl.
    *A61B 3/103*     (2006.01)
    *A61B 3/00*     (2006.01)
    *A61B 3/13*     (2006.01)
    *A61B 3/117*     (2006.01)
    *A61B 3/12*     (2006.01)

(52) U.S. Cl.
    CPC .......... *A61B 3/0075* (2013.01); *A61B 3/0091* (2013.01); *A61B 3/102* (2013.01); *A61B 3/1035* (2013.01); *A61B 3/117* (2013.01); *A61B 3/1173* (2013.01); *A61B 3/12* (2013.01); *A61B 3/13* (2013.01); *A61B 3/132* (2013.01); *A61B 3/14* (2013.01)

(56) References Cited

U.S. PATENT DOCUMENTS

| | | | |
|---|---|---|---|
| 6,043,890 | A | 3/2000 | Spink et al. |
| 7,387,385 | B2 * | 6/2008 | Sander ............... G02B 21/0012 351/206 |
| 8,049,873 | B2 | 11/2011 | Hauger et al. |
| 2013/0150840 | A1 * | 6/2013 | Sander .................... A61B 3/13 606/6 |
| 2014/0024949 | A1 | 1/2014 | Wei et al. |
| 2016/0183779 | A1 * | 6/2016 | Ren ..................... A61B 3/0058 351/206 |

FOREIGN PATENT DOCUMENTS

| | | |
|---|---|---|
| DE | 102008047400 | 4/2010 |
| DE | 202010008225 | 10/2010 |
| EP | 1602320 | 12/2005 |

* cited by examiner

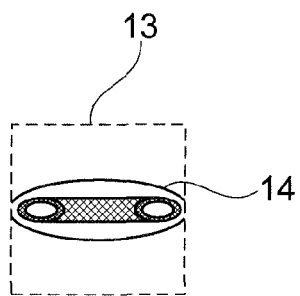
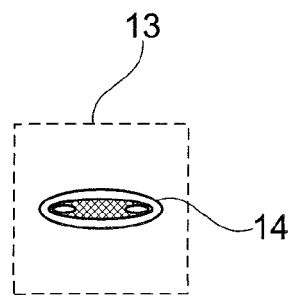
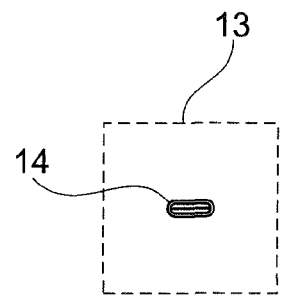
FIG. 3A    FIG. 3B    FIG. 3C
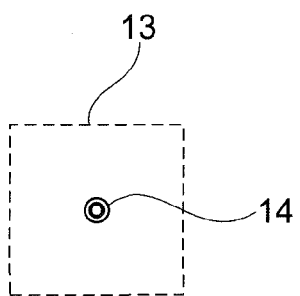
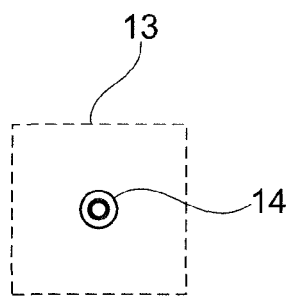
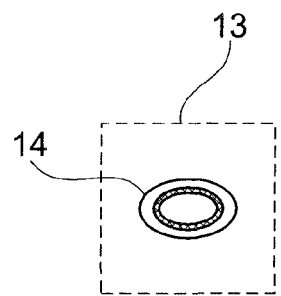
FIG. 3D    FIG. 3E    FIG. 3F

SURGICAL MICROSCOPE

CROSS REFERENCE TO RELATED APPLICATION

This application claims priority of German patent application no. 10 2015 115 106.5, filed Sep. 8, 2015, the entire content of which is incorporated herein by reference.

FIELD OF THE INVENTION

The invention relates to a surgical microscope for interventions on the anterior chamber of the eye, for example for a cataract operation.

BACKGROUND OF THE INVENTION

Surgical microscopes for ophthalmic surgery are known from the prior art, for example from DE 10300925 A1. Such surgical microscopes are usually embodied in such a way that they generate a stereoscopic image of the eye such that the surgeon obtains a spatial impression of the eye to be operated.

In ophthalmic surgery, it is important for the surgeon to know the refractive state of the eye as present at the time of the intervention. By way of example, in the case of cataract operations, the refractive properties are required if the orientation of a toric lens needs to be set. Another problem in the case of cataract operation consists of an intraocular lens being inserted, the values of which were established on the basis of measurements which were carried out prior to the surgical intervention. However, such measurements may be erroneous due to the lens opacification caused by the cataract. Therefore, it is desirable to check the refractive properties of the eye once more prior to the insertion of the intraocular lens but after the removal of the eye lens, that is, on the aphakic eye, so that the lens selection can be corrected where necessary. It is also of interest to check the refractive values of the eye directly after the completion of the operation.

The prior art has disclosed intraoperative refraction measurements, which establish the wavefront emerging from the eye via parallel or time-sequential measurement systems and determine the refractive properties of the eye therefrom. However, these measurement methods are very complicated and require that additional, complex beam paths are coupled into the eye, as a result of which the outlay required for the surgical microscope increases.

The prior art has disclosed a method referred to as "phase retrieval", which allows conclusions to be drawn about a transfer quality of an optical system by way of specific measurements.

SUMMARY OF THE INVENTION

It is an object to provide a surgical microscope with which the refractive properties of the eye can be established with little outlay.

According to the invention, this object is achieved by a surgical microscope for imaging structures of an eye, the surgical microscope including:
a front optical unit,
an illumination device which emits illumination radiation and which illuminates the retina of the eye with an illumination spot by way of an illumination beam path which extends through the front optical unit,
a camera and an adjustable camera optical unit disposed upstream thereof,
an imaging beam path which extends through the front optical unit and the camera optical unit, and
a control device which controls the camera optical unit and sets the latter in such a way that the retina of the eye in the region of the illumination spot is imaged on the camera,
wherein the control device varies a focusing state of the camera optical unit and, as a result thereof, records a plurality of images of the retina in the region of the illumination spot, the images being focused in different depth planes, and establishes a refractive value of the eye from these images.

The inventors recognized that the "phase retrieval" method, which was previously not used in ophthalmology, can be realized using a surgical microscope without substantial interventions on the existing surgical microscope being necessary. The surgical microscope should be configured in a comparatively simple manner to the extent that the refractive properties of the eye can be determined intraoperatively with the aid of the "phase retrieval" method. Here, the fact that a surgical microscope which is configured for cataract surgery usually illuminates the eye lens with a parallel beam is advantageously exploited. On account of the refractive properties of the eye, a beam which is incident in parallel onto the pupil of the eye generates an illumination spot on the retina. Such an illumination method of the eye lens for surgical microscopes is known by the term SCI illumination and realized, for example, in the surgical microscope OPMI Lumera 700 by Carl Zeiss Meditec AG.

The illumination spot is imaged with the camera of the surgical microscope, with different focusing states in the z-direction being realized. Therefore, there is a slight variation in the position of the image plane relative to the camera plane. This can be considered as "defocusing", that is, as displacement of the object plane of the video camera in relation to the plane in which the illumination spot is focused. The plurality of images obtained thus constitute a so-called focus stack; they contain the images of the illumination spot with different defocusing states. Then, an image analysis of these various images according to the "phase retrieval" method supplies a refractive value of the eye.

The illumination spot is imaged by virtue of the camera optical unit being deliberately defocused for the purposes of recording the plurality of images. This deviates from the usual procedure in microscopy, in which an image which is focused to the best possible extent is obtained. Here, in an embodiment of the invention, provision is made for the camera optical unit for recording the images of the illumination spot to be set to an object plane, independently of which object plane of the surgical microscope is set for the purposes of examining the eye by microscopy. For the purposes of establishing the refractive value, the control device sets the camera optical unit into the object plane on the retina, without also adjusting the remaining imaging channels of the surgical microscope at the same time, for example, a tube eyepiece or eyepiece or a camera of a different stereo channel.

In an embodiment of this concept, for the purposes of establishing the refractive value, the control device intermittently switches the camera optical unit onto the object plane in which the focal spot lies and it records the focus stack there but keeps the other imaging channels of the surgical microscope with such a setting that a different object plane is examined by microscopy. In this manner, the camera optical unit and the camera are switched into a multiplex operation, in which the refractive value of the eye is established repeatedly during the examination of a different region, for example, the anterior chamber of the eye or eye lens, by microscopy. Naturally, during the recording of the plurality of images required for establishing the refraction value, the camera supplies image information which does not fit to the other imaging devices, for example a different stereo channel or a tube device and eye device. Therefore, provision is made in a preferred embodiment for the surgical microscope to be provided as a stereo surgical microscope and for the camera used to establish the refractive value to be the camera of a stereo channel of the stereo surgical microscope. Here, during the time period in which the camera is directed onto an object plane which differs from the object plane of the other stereo channel, it is particularly preferable either for the microscope to be switched into monocular mode of operation or, for the duration of the determination of the plurality of images, for the image information established during synchronous operation of the two cameras to be maintained for the channel whose camera is used for establishing the refractive value. If the microscope is switched into a monocular mode of operation in respect of the cameras, one of the two cameras can be used for microscopy in the object plane desired by the user; the other camera serves for the continuous establishment of the refractive value, that is, it is set to an object plane lying in the region of the illumination spot.

The surgical microscope can also realize a further operating state, to the effect that the camera optical unit has an adjustable embodiment and, in the further operating state, the control device sets the latter in such a way that an image of the anterior chamber or the eye lens of the eye is generated. In this way, a user can easily switch between the two operating states and either sees an image of the anterior chamber/eye lens, as is conventional for a cataract intervention, or uses the operating mode in which the surgical microscope automatically establishes a refractive value of the eye via the control device. Switching to and fro between the two modes of operation provides the user with the information about the current refractive state of the eye at any time during the surgical intervention, as a result of which the result of the surgical intervention is improved overall.

The illumination spot is formed on the eye from illumination radiation incident in parallel into the anterior chamber when an eye lens is present in the eye, either the natural intraocular lens or an intraocular lens inserted by surgery. However, additional optical measures are required to form the illumination spot in the case of an aphakic eye. Therefore, it is preferable in one embodiment of the surgical microscope for provision to be made of an adjustable optical unit and/or an optical unit which can be brought into the illumination beam path, the optical unit focusing the illumination radiation in such a way that an illumination spot is formed at the retina, even in the case of an aphakic eye.

The refractive value of the eye can be established via the "phase retrieval" method, which was already specified at the outset. A simplified establishment, which possibly has a sufficient, lower accuracy, is already obtained if an outline form of the illumination spot is evaluated in the images; that is, the control device establishes what outline the illumination spot has in the various defocused images. By way of example, the principal axis of an astigmatism can be established from this outline shape. For certain requirements, the specification of the principal axis as a refractive value suffices, for example if the surgeon should be provided with assistance in respect of the orientation in which a toric intraocular lens should be inserted. Therefore, the term refractive value includes the position of the principal axis of an astigmatism in some embodiments. In other embodiments, the refractive value is the value of a spherical and/or cylindrical deviation. In further embodiments, the refractive value is a specification of Zernike polynomials.

For such applications, it is particularly advantageous if the surgical microscope has a display device and the control device establishes the astigmatism axis as refractive value and plots the latter into an image of the eye on the display device. However, such an embodiment of the surgical microscope is naturally also advantageous if specifications going beyond the astigmatism axis are established for the refractive value of the eye.

In all cases where the eye is not aphakic, that is, either the natural eye lens or eye lens inserted by surgery is present, it is preferable, in view of a constructional outlay of the surgical microscope which is as small as possible, for a beam splitter to be disposed downstream of the front optical unit, the beam splitter coupling the imaging beam path into the illumination beam path, as a result of which the illumination beam path is then embodied as a parallel beam path between the front optical unit and the eye, like the illumination beam path as well.

In such cases, it is likewise preferable for the illumination device to illuminate the eye lens with a parallel illumination beam.

The refractive value of the eye is determined particularly precisely if the illumination spot has a minimal dimension. The dimension of the illumination spot can be set by a stop which is disposed upstream of the beam splitter in the illumination beam path. The dimension thereof directly influences the dimension of the illumination spot. Here, "directly" should be understood to mean that a reduction in the dimension of the stop also reduces the illumination spot. However, the dimension of the stop also directly influences the brightness with which the anterior chamber of the eye or eye lens is illuminated. Naturally, a user would like a brightness of the illumination of the anterior chamber or eye lens which is as high as possible for the cataract operations. Therefore, it is preferable in one embodiment for the control device to adjust the dimension of the stop depending on which mode of operation is used. If the camera is set for the anterior chamber or the eye lens, the stop is set to be larger than in the operating mode in which the refractive value of the eye is established. An optimization is possible for both modes of operation by adjusting the stop.

The determination of the refractive value is only reliable if the patient looks into the measurement beam, that is, fixates thereon in an appropriate manner, during the measurement. Therefore, an embodiment in which the illumination source simultaneously serves as fixation source is preferred. Alternatively, a light spot, for example from a laser or an SLD light source, which is additionally coupled into the illumination beam path is used as a fixation light. It is particularly advantageous to select a wavelength in the short-wavelength range of the visible spectrum, for example, green, for the fixation light since an illumination spot then is smaller than in the case of radiation with a longer wavelength due to the reduced scattering in the retinal tissue.

The prior art, for example, US 2014/0024949, has disclosed the practice of additionally providing an OCT on an surgical microscope. Determining the refractive value was found to be particularly precise if the illumination spot lies as close as possible to the fovea. It is therefore preferable for the surgical microscope to additionally have an OCT (Optical Coherence Tomography), which is likewise controlled by the control device and the measured values of which are read by the control device, and for the control device only to establish the refractive value of the eye if the measured values of the OCT indicate that the illumination spot lies within predetermined surroundings of the fovea or directly on the fovea. Checking whether the illumination spot lies sufficiently close, or on, the fovea is known to the control device in the surgical microscope since the geometric relation between the beam path of the OCT and the illumination beam path is set and known. In this way, it is possible to ensure that the refractive value is only established when the eye is in a correct fixation state.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
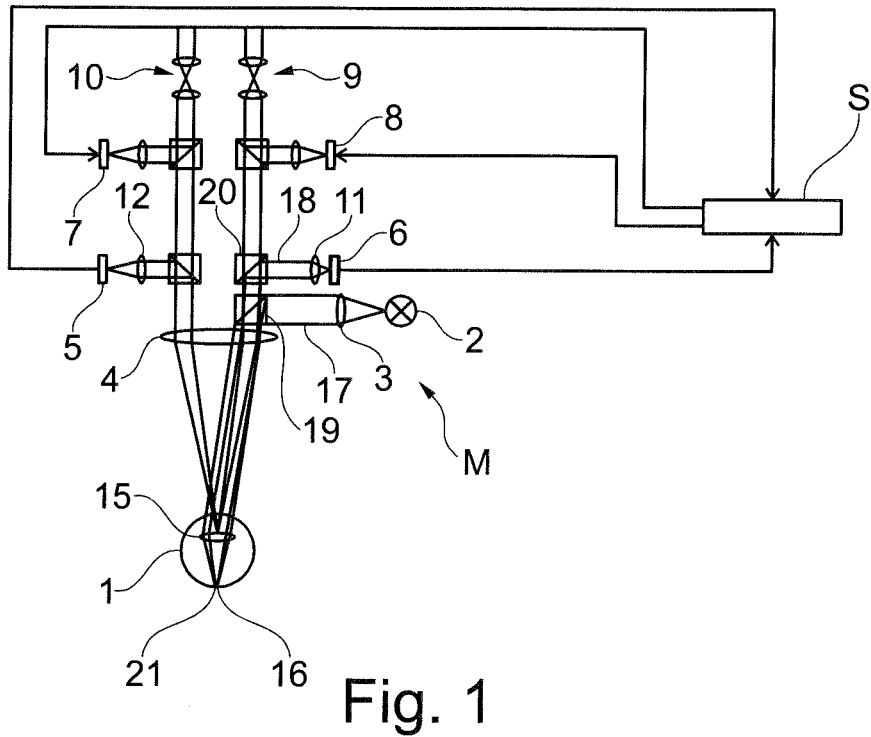
FIG. 1 shows a surgical microscope which images an eye for establishing a refractive value of the eye.

FIG. 1 shows a surgical microscope M which is embodied for imaging an eye 1 during a surgical intervention, in this case a contract operation. The surgical microscope M illuminates the eye 1 with light from a light source 2, which may be, for example, a halogen lamp, a xenon arc lamp, an LED, a laser or an SLD. An illumination optical unit 3 focuses the illumination radiation emanating from the light source 2 in such a way that, in combination with a main objective, a parallel beam is incident on the eye 1. An eye lens 15 of the eye 1 brings about focusing of this parallel illumination beam onto an illumination spot 16. The illumination optical unit 3 and the front optical unit and the main objective 4 therefore set an illumination beam path 17, which runs over a beam splitter 19 in order to connect the illumination beam path 17 with an imaging beam path of the surgical microscope M.

The surgical microscope M images the eye 1 on cameras (5, 6) by way of the main objective 4, the cameras supplying their data to a control device S. The control device S can, for example, be or include a processor, CPU, electrical control circuit, computer, computer processor, a microprocessor or the like. The control device may include a memory/data storage unit. The cameras (5, 6) are coupled on by way of a beam splitter such that the surgical microscope M supplies a stereo image of the eye 1, even in a tube and eyepiece optical unit (9, 10). Additionally, displays (7, 8) are mirrored-in by way of beam splitters such that a user sees not only a stereo image of the eye 1 but also image information originating from the displays (7, 8) when looking in through the tube and eyepiece optical unit (9, 10). The displays are likewise supplied with appropriate data by the control device S.

In the illustration of FIG. 1, the eye 1 has an eye lens 15, that is, it is not in an aphakic state which may occur during the cataract operation. As a result, the illumination radiation incident in parallel is focused into the illumination spot 16. Overall, the eye lens 15 participates in the illumination beam path 17. If the eye does not have an eye lens 15, an adjustment of the illumination optical unit 3 is provided, the latter ensuring that the illumination spot 16 nevertheless arises on the retina of the eye 1.

The eye is imaged on the camera 6 by way of an imaging beam path 18, which is formed, inter alia, by the main objective 4 and the camera optical unit 11. Here, under the control of the control device S, the camera optical unit 11 is adjustable in such a way that a focus 21 of the image lies on the retina and hence at the location of the illumination spot 16. The illumination spot 16 and the focus 21 coincide spatially since the imaging beam path 18 to the camera 6 is coupled into the illumination beam path 17 by way of the beam splitter 19. The incidentally still plotted beam splitter 20 separates the imaging beam path onto the camera 6 from the imaging beam path onto the tube and eyepiece optical unit. This could also be inverted, that is, the beam splitter 20 separates the radiation for the tube and eyepiece optical unit (9, 10). Since both the imaging beam path 18 and the illumination beam path 17 run through the objective 4, an image of the illumination spot 16 arises on the camera 6. In order to establish a refractive value of the eye 1, the control device S sets the camera optical unit 11 into different positions and records a series of images 13, which are shown in FIGS. 3A to 3F. The images 13 correspond to different focusing states, that is, different displacements of the image plane defined by the imaging beam path 18 and of the plane in which the camera 6 is situated. FIG. 3A corresponds to defocusing of −4 mm, FIG. 3B corresponds to defocusing of −2 mm, FIG. 3C corresponds to a focusing state of 0 mm, that is, the image plane and the plane of the camera 6 coincide in this case, FIG. 3D corresponds to defocusing of +2 mm, FIG. 3E corresponds to defocusing of +4 mm and FIG. 3F corresponds to defocusing of +6 mm.

As shown in FIGS. 3A to 3F, the form of an illumination spot image 14 in the images 13 changes depending on the defocusing. The plurality of images 13 recorded in this manner by the control device S corresponds to a focus stack. The control device S calculates a refractive value of the eye therefrom. As explained in the general part of the description, the refractive value can merely specify the position of the principal axis of the astigmatism in the simplest case. In an embodiment, a qualitative measure for refractive error is also determined from the focus stack, for example in the form of Zernike polynomials.

Figure 2:
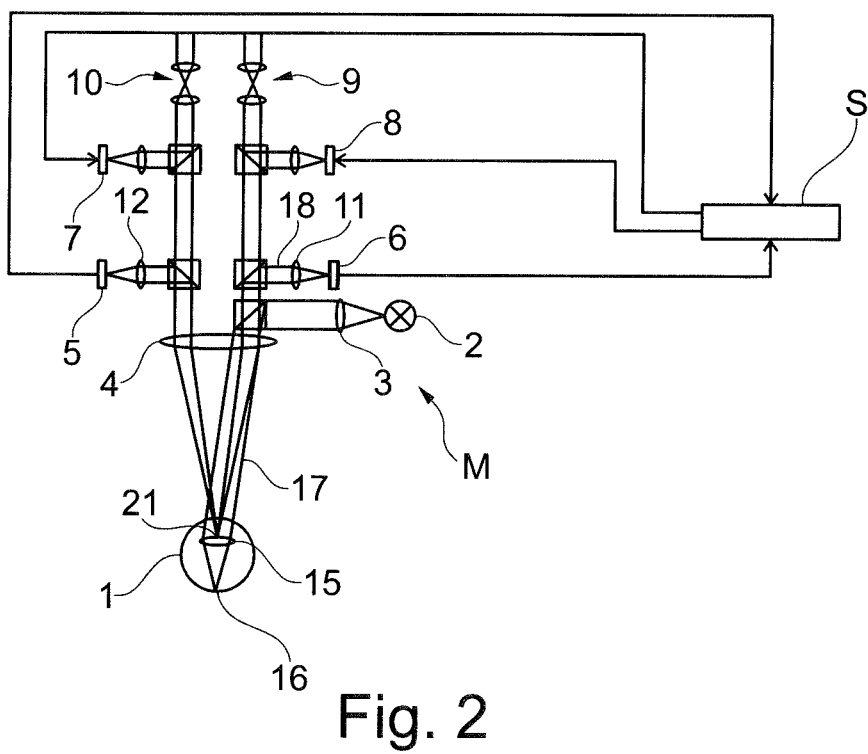
FIG. 2 shows the surgical microscope from FIG. 1 in a different operating state, in which an eye lens of the eye is imaged; and, FIGS. 3A to 3F show a plurality of images which were recorded by the surgical microscope in the operating state of FIG. 1 in order to establish the refractive value of the eye.

FIG. 2 shows a further operating state of the surgical microscope M, in which the focus 21 lies in the anterior chamber or at the eye lens 15. This is achieved by virtue of the control device S accordingly setting the camera optical unit 11 in such a way that the object plane of the imaging beam path 18 lies or in the region of the eye lens 15.

In other words, the control device S sets the camera optical unit 11 for the further operating mode in such a way that a different plane is conjugate to the plane of the camera 6, namely the desired plane in the region of the eye lens 15 or in the anterior chamber. By contrast, in the operating mode of FIG. 1, the camera optical unit 11 is set in such a way that the camera 6 is conjugate to a plane in which the retina lies.

Naturally, the second camera 5 and the mirroring-in of the data from the display (7, 8) are optional.

The illustrations of FIGS. 3A to 3F show the change in the spot form depending on the defocusing of the camera optical unit 11 for an astigmatic error of the eye of 1 diopter, wherein the focal length of the main objective is 200 mm and the focal length of the camera optical unit 11 is 50 mm.

The illumination spot 16 on the retina can also be generated differently to what is depicted in FIGS. 1 and 2. As an alternative to the SCI illumination used there, it is also possible to use a laser light source or an SLD light source coupled into the beam path, as is known, for example, for realizing an OCT in surgical microscopes.

The camera optical unit 11 allows the control device S to switch between the modes of operation of FIG. 1 and FIG. 2, that is, to place the object planes imaged on the camera 6 in the region of the eye lens or in the region of the retina, depending on the setting of the camera optical unit 11. This adjustment possibility permits the integration of the determination of the refractive values of the eye 1 into the surgical microscope M.

In order to generate an illumination spot 16 on the retina 1 which is as small as possible, it is preferable to dispose a stop (not depicted in FIGS. 1 and 2) in front of the light source 2 and to set the spot differently for determining the refractive value or for imaging the eye lens, as was already explained in the general part of the description.

Intraoperative refraction measurements are only reliable if the patient looks into the measurement beam during the measurement. The fixation sources mentioned in the general part of the description are therefore advantageous for an optional embodiment of the surgical microscope M. If an OCT system is used for fixation or illumination, care has to be taken that visible radiation, that is, light, is coupled into the OCT interferometer.

For the purposes of aligning a toric lens during the cataract operation, the refractive value of the eye must be established virtually in real time so that the surgeon rotates the toric intraocular lens under control of the surgical microscope M, that is, with the current display of the refractive value, for example the principal axis of the astigmatism. Therefore, an embodiment in which the control device S places the surgical microscope M to and fro between the two modes of operation in a multiplex mode is preferred, that is, in which the control device alternately shifts the camera optical unit 11 between two basic positions, in which the object plane lies in the region of the eye lens and in the region of the retina, respectively, and records the focus stack for the basic position with the position of the object plane in the region of the retina.

An embodiment of the multiplex operation includes one of the two cameras, for example, the camera 6, being set in terms of the camera optical unit thereof, in this case the camera optical unit 11, in such a way that the refractive value of the eye is determined, while the other camera, for example, the camera 5, is set in terms of the camera optical unit thereof, in this case the camera optical unit 12, in such a way that the object plane lies in the region of the eye lens 15. Therefore, there is a deliberate difference in the settings of the camera optical units (11, 12) assigned to the stereo channels, which are always set the same during stereo operation. The deliberate deviation from the prescription of the stereo operation renders it possible to continuously establish the refractive value, as already explained in the general part of the description.

The "phase retrieval" method renders it possible to measure the properties of the whole optical system including eye and surgical microscope M. Provision is therefore made in an embodiment for the optical properties of the surgical microscope M to be measured and accordingly subtracted from the measurement result such that only the optical properties of the eye 1 are established as refractive value.

In place of the integration into the beam path of the surgical microscope M, shown in FIGS. 1 and 2, provision can also be made of a separate module below the main objective 4, the separate module including a camera for recording the focus stack and the adjustable camera optical unit required therefor. Either a light source used in the surgical microscope M or a light source integrated into the additional module can be used as a light source for generating the illumination spot.

The position of the principal axis of an astigmatism can be established from the outline shape of the illumination spot image 14. For this, two images are already sufficient, that is, a focus stack having two images 13.

For the purposes of generating the focus stack, provision is made in one embodiment of a lens with a variable focal length and without mechanically moving elements being used instead of an adjustment of the camera optical unit 11, the lens particularly preferably only being provided in the camera optical unit 11 for the adjustment for recording the focus stack.

It is understood that the foregoing description is that of the preferred embodiments of the invention and that various changes and modifications may be made thereto without departing from the spirit and scope of the invention as defined in the appended claims.

What is claimed is:

1. A surgical microscope for imaging structures of an eye, the surgical microscope comprising:
   a front optical unit;
   an adjustable camera optical unit;
   the surgical microscope defining an illumination beam path extending through said front optical unit and an imaging beam path extending through said front optical unit and said adjustable camera optical unit;
   an illumination device having an illumination-radiation-emitting illumination source and being configured to illuminate the retina of the eye with an illumination spot via said illumination beam path;
   a camera;
   said adjustable camera optical unit being disposed upstream of said camera with respect to said imaging beam path;
   a control device configured to control said adjustable camera optical unit and set said adjustable camera optical unit so as to cause the retina of the eye to be imaged on said camera in the region of said illumination spot;
   said control device being further configured to vary a focusing state of said adjustable camera optical unit and to record a plurality of images of the retina of the eye in the region of the illumination spot via said camera, said images being focused in different depth planes; and,
   said control device being further configured to establish a refractive value of the eye from said images.

2. The surgical microscope of claim 1, wherein:
   said illumination spot defines an outline shape; and,
   said control device is further configured to evaluate said outline shape of said illumination spot in said images.

3. The surgical microscope of claim 1, further comprising: a beam splitter disposed downstream of said front optical unit with respect to said imaging beam path; and, said beam splitter being configured to couple said imaging beam path into said illumination beam path.

4. The surgical microscope of claim 3, wherein said imaging beam path is formed as a parallel beam path between said front optical unit and the eye.

5. The surgical microscope of claim 1, wherein:
said illumination device being further configured to simultaneously illuminate a lens of the eye via a parallel illumination beam; and,
said control device being further configured to provide an additional mode of operation of the surgical microscope via setting said adjusting camera optical unit so as to cause at least one of the lens of the eye and an anterior chamber of the eye to be imaged on said camera.

6. The surgical microscope of claim 5, further comprising: a beam splitter disposed downstream of said front optical unit with respect to said imaging beam path; said beam sputter being configured to couple said imaging beam path into said illumination beam path; an adjustable stop disposed upstream of said beam splitter with respect to said illumination beam path; said adjustable stop having dimensions which directly influence the dimension of said illumination spot and simultaneously a brightness of an illumination of the anterior chamber or of the lens of the eye; and, said control device being configured to set said adjustable stop to be smaller for establishing said refractive value of the eye than in the case of said additional mode of operation.

7. The surgical microscope of claim 1, wherein said illumination-radiation-emitting illumination source is configured to simultaneously serve as a fixation light.

8. The surgical microscope of claim 1, wherein said illumination-radiation-emitting illumination source emits green illumination light.

9. The surgical microscope of claim 1, further comprising: an OCT unit; said control device is further configured to control said OCT unit and read out measurement values from said OCT unit; and, said control device being configured to establish said refractive value of said eye only if said measurement values indicate that said illumination spot lies within a predetermined perimeter around the fovea or on the fovea.

10. The surgical microscope of claim 1, further comprising: a display device configured to display an image of the eye; and, said control device being configured to establish an astigmatism axis as refractive value and plots said astigmatism axis into said image of the eye displayed by said display device.

11. The surgical microscope of claim 1, wherein the surgical microscope is configured as a stereo surgical microscope; and, said camera is a first camera, the surgical microscope further comprising:
a second camera;
said first and said second cameras being configured as two stereo channel cameras; and,
said control device being configured to at least intermittently switch the stereo operating microscope into a monocular mode of operation with respect to said stereo channel cameras by virtue of focusing said adjustable camera optical unit onto said illumination spot and focusing said second camera onto a different object plane.

12. A surgical microscope for imaging structures of an eye, the surgical microscope comprising:
a front optical unit including at least one lens;
an adjustable camera optical unit having at least one lens;
the surgical microscope defining an illumination beam path extending through said front optical unit and an imaging beam path extending through said front optical unit and said adjustable camera optical unit;
an illumination device having an illumination-radiation-emitting illumination source and being configured to illuminate the retina of the eye with an illumination spot via said illumination beam path;
a camera;
said adjustable camera optical unit being disposed upstream of said camera with respect to said imaging beam path;
a control device configured to control said adjustable camera optical unit and set adjustable said camera optical unit so as to cause the retina of the eye to be imaged on said camera in the region of said illumination spot;
said adjustable camera optical unit being further configured to define a plurality of focusing states of said adjustable camera optical unit;
said control device being further configured to vary said focusing state of said adjustable camera optical unit and to record a plurality of images of the retina in the region of the illumination spot via said camera;
said images being focused in different depth planes; and,
said control device being further configured to establish a refractive value of the eye from said images.

* * * * *